(12) United States Patent
Saito et al.

(10) Patent No.: US 9,963,724 B2
(45) Date of Patent: May 8, 2018

(54) METHOD FOR PRODUCING 5-AMINOLEVULINIC ACID OR SALT THEREOF

(71) Applicant: neo ALA Co., Ltd., Minato-ku (JP)

(72) Inventors: Masaru Saito, Satte (JP); Taishi Yamamoto, Satte (JP); Haruki Kawano, Satte (JP)

(73) Assignee: neo ALA Co., Ltd., Minato-ku (JP)

( * ) Notice: Subject to any disclaimer, the term of this patent is extended or adjusted under 35 U.S.C. 154(b) by 0 days. days.

(21) Appl. No.: 14/778,916

(22) PCT Filed: Mar. 19, 2014

(86) PCT No.: PCT/JP2014/057500
§ 371 (c)(1),
(2) Date: Sep. 21, 2015

(87) PCT Pub. No.: WO2014/148539
PCT Pub. Date: Sep. 25, 2014

(65) Prior Publication Data
US 2016/0046969 A1 Feb. 18, 2016

(30) Foreign Application Priority Data

Mar. 22, 2013 (JP) .................. 2013-059431
Mar. 22, 2013 (JP) .................. 2013-059432
Jan. 21, 2014 (JP) .................. 2014-008197

(51) Int. Cl.
C12P 13/00 (2006.01)
C12N 1/00 (2006.01)

(52) U.S. Cl.
CPC .............. *C12P 13/005* (2013.01); *C12N 1/00* (2013.01)

(58) Field of Classification Search
None
See application file for complete search history.

(56) References Cited

U.S. PATENT DOCUMENTS

| 5,733,770 | A | 3/1998 | Watanabe et al. |
| 5,763,235 | A | 6/1998 | Watanabe et al. |
| 6,342,377 | B1 | 1/2002 | Nishikawa et al. |
| 2009/0036709 | A1 | 2/2009 | Okada et al. |

FOREIGN PATENT DOCUMENTS

| EP | 0 718 405 A2 | 6/1996 |
| EP | 1 018 546 A1 | 7/2000 |
| JP | 61-502814 A | 12/1986 |
| JP | 2-138201 A | 5/1990 |
| JP | 2-261389 A | 10/1990 |
| JP | 6-141875 A | 5/1994 |
| JP | 6-153915 A | 6/1994 |
| JP | 8-168391 A | 7/1996 |
| JP | 11-42083 A | 2/1999 |
| JP | 2007-84466 A | 4/2007 |
| JP | 2008-29272 A | 2/2008 |
| WO | 86/00785 A1 | 2/1986 |

OTHER PUBLICATIONS

Li et al. 5-Aminolevulinic Acid Synthesis in *Escherichia coli*. Journal of Bacteriology (1989), v171(5), p. 2547-2552.*
BD BionutrientsTM Technical Manual (3rd Edition, published 2006, 72 pages.*
Nishikawa et al. Rhodobacter sphaeroides Mutants Which Accumulate 5-Aminolevulinic Acid under Aerobic and Dark Conditions. Journal of Bioscience and Bioengineering (1999), v87(6), p. 798-804.*
Sasaki et al. Biosynthesis, biotechnological production and applications of 5-aminolevulinic acid. Appl Microbiol Biotechnol (2002), v58, p. 23-29. (Year: 2002).*
International Search Report and Written Opinion of the International Searching Authority dated May 13, 2014 in PCT/JP14/057500 Filed Mar. 19, 2014.
International Preliminary Report on Patentability and Written Opinion dated Sep. 22, 2015 in PCT/JP2014/057500.
Extended European Search Report dated Oct. 5, 2016 in Patent Application No. 14768007.8.
Ken Sasaki et al., "Production of 5-Aminolevulinic Acid by Photosynthetic Bacteria", Journal of Fermentation Technology vol. 65, No. 5, 1987, pp. 511-515.
K. Sasaki et al., "Effect of Culture pH on the Extracellular Production of 5-Aminolevulinic Acid by Rhodobacter Sphaeroides from Volatile Fatty Acids", Biotechnology Letters, 1993, vol. 15, No. 8, pp. 859-864.

* cited by examiner

*Primary Examiner* — Sean C. Barron
(74) *Attorney, Agent, or Firm* — Oblon, McClelland, Maier & Neustadt, L.L.P.

(57) ABSTRACT

Provided is a method for producing 5-aminolevulinic acid or a salt thereof at a high yield using 5-aminolevulinic acid-producing microorganisms. The method for producing 5-aminolevulinic acid or a salt thereof comprises culturing 5-aminolevulinic acid-producing microorganisms in a medium comprising one or more components selected from the group consisting of L-arginine, glutamic acid, and a salt thereof. The content of glutamic acid or the salt thereof is from 42 to 100 mM in the medium as the glutamic acid.

9 Claims, No Drawings

METHOD FOR PRODUCING 5-AMINOLEVULINIC ACID OR SALT THEREOF

TECHNICAL FIELD

The present invention relates to a method for efficiently producing 5-aminolevulinic acid or a salt thereof using microorganisms.

BACKGROUND ART

5-Aminolevulinic acid is widely present in the biosphere as a metabolic intermediate in the pigment biosynthetic pathway biosynthesizing tetrapyrrole compounds (such as vitamin $B_{12}$, heme, and chlorophyll) and plays important roles in vivo. 5-Aminolevulinic acid is biosynthesized in biological systems from glycine and succinyl CoA by means of a 5-aminolevulinic acid synthase or from glutamic acid through glutamyl tRNA and is converted into porphyrin compounds such as heme or chlorophyll by means of metabolism following 5-aminolevulinic acid dehydratase. This 5-aminolevulinic acid is highly degradable and substantially does not remain in the environment and is therefore expected to be applied to a variety of industries (Patent Literatures 1 and 2).

A method using a variety of photosynthetic bacteria, in particular, bacteria belonging to *Rhodobacter* or variants thereof is known as the method for producing 5-aminolevulinic acid or a salt thereof using microorganisms (Patent Literatures 3 and 4). In addition, for example, a method of culturing such microorganisms under oxygen-limited conditions (Patent Literature 5), a method using a variant producing 5-aminolevulinic acid under moderated conditions of the oxygen-limited conditions (Patent Literature 6), and a method using an established oxygen condition (Patent Literature 7) have been reported.

Although culturing conditions have been reported as described above, there have been no reports on culture media and productivity improvers for increasing productivity excepting the description on the amount of iron (Patent Literature 6).

In general, 5-aminolevulinic acid or the salt thereof produced by microorganism culture described above can be optionally isolated and purified in accordance with a usual method such as ion exchange chromatography or extraction. In order to achieve high purification, a method for isolating 5-aminolevulinic acid from a culture solution using a cation exchange resin is known (Patent Literature 8). The purification of 5-aminolevulinic acid using a cation exchange resin is affected by a by-product, 5-amino-4-hydroxypentanoic acid of Formula (1). That is, since this 5-amino-4-hydroxypentanoic acid has a pKa value and a pI value that are very close to those of 5-aminolevulinic acid, in purification by ion exchange chromatography, 5-amino-4-hydroxypentanoic acid and 5-aminolevulinic acid compete for exchange groups of the ion exchange resin. Accordingly, achievement of high purification of 5-aminolevulinic acid requires use of an ion exchange resin in a large amount relative to the amount of 5-aminolevulinic acid passing through the resin. Therefore, inhibition of the accumulated amount of 5-amino-4-hydroxypentanoic acid in the culture solution is effective for increasing the efficiency of high purification of 5-aminolevulinic acid by ion exchange chromatography.

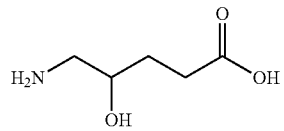

(1)

CITATION LIST

Patent Literatures

[Patent Literature 1] JP-A-S61-502814
[Patent Literature 2] JP-A-H02-138201
[Patent Literature 3] JP-A-H06-141875
[Patent Literature 4] JP-A-H06-153915
[Patent Literature 5] JP-A-H08-168391
[Patent Literature 6] JP-A-H11-42083
[Patent Literature 7] JP-A-2008-29272
[Patent Literature 8] JP-A-2007-84466

SUMMARY OF INVENTION

Technical Problem

As described above, a variety of methods for producing 5-aminolevulinic acid or a salt thereof have been investigated, but a further improvement in yield is desired.

It is an object of the present invention to provide a method for producing 5-aminolevulinic acid or a salt thereof at a high yield using 5-aminolevulinic acid-producing microorganisms.

Further provided is a method for inhibiting accumulation of 5-amino-4-hydroxypentanoic acid in a culturing process.

Solution to Problem

Under the circumstances, a variety of studies on conditions, in particular, medium components, for culturing 5-aminolevulinic acid-producing microorganisms has been performed. As a result, it has been found that 5-aminolevulinic acid or a salt thereof can be produced at a higher yield than by conventional methods, by culturing 5-aminolevulinic acid-producing microorganisms in a medium comprising L-arginine, a predetermined amount of glutamic acid, or a salt thereof, in addition to common nutrient components such as yeast extract.

Furthermore, it has been found that accumulation of 5-amino-4-hydroxypentanoic acid can be inhibited by culturing 5-aminolevulinic acid-producing microorganisms in a medium comprising L-arginine, a certain amount of glutamic acid, or a salt thereof, in addition to common nutrient components such as yeast extract. Thus, the present invention has been accomplished.

That is, the present invention provides the following [1] to [6]:

[1] A method for producing 5-aminolevulinic acid or a salt thereof, comprising culturing a 5-aminolevulinic acid-producing microorganism in a medium comprising one or more components selected from L-arginine, glutamic acid, and a salt thereof, wherein a content of glutamic acid or the salt thereof is from 42 to 100 mM as the glutamic acid in the medium;

[2] The method for producing 5-aminolevulinic acid or a salt thereof according to [1], wherein a content of L-arginine or the salt thereof is 0.5 to 15 mM as the L-arginine in the medium;

[3] The method for producing 5-aminolevulinic acid or a salt thereof according to [1] or [2], wherein a content of L-arginine or the salt thereof is 0.01 to 30 mM as the L-arginine in the medium;

[4] The method for producing 5-aminolevulinic acid or a salt thereof according to any one of [1] to [3], wherein the 5-aminolevulinic acid-producing microorganism belongs to *Rhodobacter*;

[5] The method for producing 5-aminolevulinic acid or a salt thereof according to any one of [1] to [4], wherein the 5-aminolevulinic acid-producing microorganism is *Rhodobacter sphaeroides* or a variant thereof; and

[6] The method for producing 5-aminolevulinic acid or a salt thereof according to any one of [1] to [5], wherein the 5-aminolevulinic acid-producing microorganism is a microorganism named *Rhodobacter sphaeroides* CR-0072009 and deposited under FERM BP-6320.

Advantageous Effect of Invention

The method of the present invention can produce 5-aminolevulinic acid or a salt thereof at a high yield by culturing 5-aminolevulinic acid-producing microorganisms in a medium comprising L-arginine, from 42 to 100 mM glutamic acid, or a salt thereof.

Furthermore, the accumulated amount of 5-amino-4-hydroxypentanoic acid, a by-product affecting the purification of 5-aminolevulinic acid or a salt thereof, can be inhibited by culturing 5-aminolevulinic acid-producing microorganisms in a medium comprising L-arginine, from 42 to 100 mM glutamic acid, or a salt thereof.

DESCRIPTION OF EMBODIMENTS

The method for producing 5-aminolevulinic acid or a salt thereof according to the present invention is characterized by the use of a medium comprising one or more components selected from L-arginine, glutamic acid, and a salt thereof (in the case of glutamic acid or a salt thereof, the amount is from 42 to 100 mM as the glutamic acid).

The content of L-arginine or the salt thereof in the medium is preferably from 0.01 to 30 mM, more preferably from 0.1 to 20 mM, still more preferably from 0.3 to 15 mM, and most preferably from 0.5 to 15 mM as the L-arginine, from the viewpoint of the productivity of 5-aminolevulinic acid and inhibition of accumulation of 5-amino-4-hydroxypentanoic acid. Examples of the salt of L-arginine include a mineral acid salt such as hydrochloride.

The content of glutamic acid or the salt thereof in the medium is characteristically higher than the concentrations in a known medium and is preferably from 42 to 100 mM, more preferably from 47 to 90 mM, and most preferably from 48 to 80 mM as the glutamic acid, from the point of productivity of 5-aminolevulinic acid.

In the present invention, the term "as the glutamic acid" and the term "as the L-arginine" mean that the concentrations of salts and hydrates of these compounds are calculated by converting the concentrations into those of glutamic acid and L-arginine, respectively. Examples of the salts of glutamic acid include alkali metal salts of glutamic acid, such as sodium glutamate. Examples of the salts of L-arginine include arginine salts of mineral salts, such as L-arginine hydrochloride.

In the method of the present invention, L-arginine, glutamic acid, or a salt thereof may be added to a culture medium at the time of preparing the medium. Preferably, L-arginine, glutamic acid, or a salt thereof may be sterilized separately from a culture medium and be added to the medium immediately before the start of production of 5-aminolevulinic acid by microorganisms. Here, the time immediately before the start of production of 5-aminolevulinic acid by microorganisms is preferably from 10 to 45 hours after the start of incubation, more preferably from 15 to 40 hours after the start of incubation, and most preferably from 20 to 35 hours after the start of incubation.

The 5-aminolevulinic acid-producing microorganisms used in the method of the present invention are photosynthetic bacteria being prokaryotic microorganisms, and examples thereof include *Rhodobacter* microorganisms and Rhodopseudomonas microorganisms. The microorganisms are preferably those belonging to *Rhodobacter*, more preferably *Rhodobacter sphaeroides* or variants thereof, and still more preferably, microorganisms named *Rhodobacter sphaeroides* CR-0072009 and deposited under FERM BP-6320.

The medium used in the present invention preferably contains at least one component selected from yeast extract, dried yeast, peptone, polypeptone, meat extract, fish meal, casamino acid, corn steep liquor (CSL), and potato dextrose broth (PDB). Among these components, at least one component selected from yeast extract and dried yeast, in particular, yeast extract is preferable. The content of these components is 1 g/L or more, more preferably from 1 to 20 g/L, and most preferably from 5 to 10 g/L, in total.

Furthermore, the culture medium for the method of the present invention preferably contains an appropriate amount of a carbon source and a nitrogen source that can be utilized by microorganisms. Usable examples of the carbon source include saccharides, such as glucose, and acids, such as acetic acid, malic acid, lactic acid, and succinic acid. Usable examples of the nitrogen source include inorganic nitrogen sources, for example, ammonia nitrogen compounds, such as ammonia, ammonium sulfate, ammonium chloride, and ammonium phosphate, and nitrate nitrogen compounds, such as sodium nitrate and potassium nitrate; and organic nitrogen compounds, such as urea, polypeptone, and yeast extract.

The culture medium for the method of the present invention can further appropriately contain, for example, an amino acid such as alanine, valine, leucine, isoleucine, proline, phenylalanine, tryptophan, methionine, glycine, serine, threonine, cysteine, glutamine, asparagine, tyrosine, lysine, histidine, or aspartic acid.

In the present invention, the medium preferably further contains minor components, such as an inorganic salt, in particular, a product prepared by heating at 100° C. or more or pressurizing at 0.1 MPa or more a mixture including a phosphorus compound, a manganese compound, and an iron compound, from the viewpoint of improving the productivity of 5-aminolevulinic acid. The phosphorus compound may be any compound containing a phosphorus element, and preferred examples thereof include phosphoric acid, phosphates, and pyrophosphoric acid. More specifically, examples of the phosphorus compound include calcium phosphate (e.g., $Ca_{10}(PO_4)_6(OH)_2$ and $Ca_3(PO_1)_2$), monosodium phosphate, disodium phosphate, pyrophosphoric acid, monoammonium phosphate, diammonium phosphate, monopotassium phosphate, dipotassium phosphate, iron phosphate, and manganese phosphate. Particularly preferred are calcium phosphate and pyrophosphoric acid.

The manganese compound may be any compound containing a manganese element, and preferred examples thereof include the manganese element contained in heterotrophic sources, a manganese salt of acid, and a manganese halide. More specifically, examples of the manganese compound include Mn-containing yeast extract, anhydrous manganese sulfate, manganese sulfate pentahydrate, manganese chloride, manganese nitrate, manganese carbonate, and manganese dioxide; and particularly preferred are Mn-containing yeast extract, anhydrous manganese sulfate, and manganese sulfate pentahydrate.

The iron compound may be any compound containing an iron element, and preferred examples thereof include an iron salt of acid, iron halide, and iron sulfide. More specifically, examples of the iron compound include EDTA-iron, iron(II) chloride and hydrates thereof, iron(III) chloride and hydrates thereof, iron sulfide, iron citrate, ammonium iron sulfate, iron acetate, iron bromide, iron lactate, iron nitrate, iron sulfate, iron phosphate, iron ammonium citrate, iron oxalate, and iron ammonium oxalate. Particularly preferred are iron (II) chloride and iron(III) chloride.

The mixture to be heated or pressurized may include a medium. The medium is, for example, a liquid substantially not containing any medium component, and is preferably water.

The heating of the mixture is performed at 100° C. or more, and the heating temperature is preferably from 110° C. to 130° C. The pressurizing of the mixture is performed at 0.1 MPa or more, and the applied pressure is preferably from 0.13 to 0.20 MPa. The mixture is preferably heated and pressurized. Such heating and pressurizing are required to be performed after mixing of a phosphorus compound, a manganese compound, and an iron compound. The heating and pressurizing before mixing cannot provide an excellent effect of enhancing proliferation of 5-aminolevulinic acid-producing microorganisms and an effect sufficiently improving the activities of the microorganisms, such as 5-aminolevulinic acid-producing ability and oxidase activity. The time of heating or pressurizing is preferably from 10 to 30 min.

In addition, in the production method of the present invention, glycine or levulinic acid is preferably added to the medium. The amount of glycine is preferably from 10 to 1000 mM, in particular, from 10 to 400 mM, based on the total amount of the medium. The amount of glycine added each time is preferably from 10 to 200 mM based on the total amount of the medium, and glycine in such an amount is preferably added several times. The amount of levulinic acid is preferably from 0.01 to 20 mM, in particular, from 0.1 to 10 mM, based on the total amount of the medium. The addition of glycine and levulinic acid may reduce the proliferation rate of 5-aminolevulinic acid-producing microorganisms. Accordingly, in such a case, glycine and levulinic acid are preferably added at the time when microorganisms have proliferated to some extent.

The incubation temperature and the pH of the medium may be those at which 5-aminolevulinic acid-producing microorganisms grow. For example, the culture temperature is preferably from 10° C. to 40° C., in particular, from 20° C. to 35° C. The pH of the medium is preferably from 4 to 9, in particular, from 5 to 8. If the pH varies during incubation, the pH is preferably adjusted with an alkali solution such as sodium hydroxide, ammonia or potassium hydroxide, or an acid such as hydrochloric acid, sulfuric acid or phosphoric acid. The incubation is not necessarily performed with photoirradiation.

5-Aminolevulinic acid or a salt thereof thus obtained in the culture solution can be purified by an ordinary method. For example, 5-aminolevulinic acid or the salt thereof can be optionally isolated and purified by an ordinary method such as ion exchange chromatography or extraction, and it is preferable to roughly purify 5-aminolevulinic acid by cation exchange resin treatment and then to remove impurities and simultaneously collect high-purity 5-aminolevulinic acid or the salt thereof by a crystallization process. The culture solution obtained by the present invention contains a high concentration of 5-aminolevulinic acid, whereas accumulation of 5-amino-4-hydroxypentanoic acid is inhibited, which therefore makes purification easy. Examples of the salt of 5-aminolevulinic acid include a hydrochloride, a phosphate, a nitrate, and the like.

EXAMPLES

The present invention will now be described in detail with reference to examples. These examples are merely intended to be illustrations, and the present invention is not limited thereto.

Production Example 1

Medium 1 (200 mL, formula is shown in Table 1) was placed in a 2-L conical flask and was sterilized at 121° C. for 20 min, followed by being cooled. *Rhodobacter sphaeroides* CR0072009 (FERN BP-6320) was inoculated in the Medium 1. The mixture was incubated with shaking at 32° C. in a dark place for 24 hours.

TABLE 1

| Medium 1 | Concentration (g/L) |
|---|---|
| Sodium L-glutamate monohydrate | 7.6 |
| $Na_2HPO_4$ | 1.73 |
| $NaH_2PO_4$ | 0.94 |
| $(NH_4)_2HPO_4$ | 1.6 |
| $MgSO_4 \cdot 7H_2O$ | 0.4 |
| $CaCl_2 \cdot 2H_2O$ | 0.106 |
| Mn-containing yeast extract | $10.9 \times 10^{-3}$ |
| Nicotinic acid | $2.0 \times 10^{-3}$ |
| (+)-Biotin | $2.0 \times 10^{-5}$ |
| Thiamine hydrochloride | $2.0 \times 10^{-3}$ |
| Yeast extract | 3 |
| $FeCl_3 \cdot 6H_2O$ | $5.44 \times 10^{-3}$ |
| Glucose | 27 |

The resulting culture was inoculated again in 200 mL of Medium 1 prepared in a 2-L conical flask such that the initial bacterial concentration (OD: 660 nm) was 0.2 and was subjected to incubation with agitation at 32° C. in a dark place for 24 hours.

Comparative Example 1

The culture obtained in Production Example 1 was inoculated in Medium 2 (30 mL, formula is shown in Table 2) prepared in a 300-mL conical flask such that the initial bacterial concentration (OD: 660 nm) was 0.5 and was subjected to incubation with agitation at 28° C. in a dark place for 24 to 26 hours. Subsequently, glycine and levulinic acid were added so as to give concentrations of 60 mM and 5 mM, respectively. After adjustment of pH in the range from 6.4 to 6.5 with sulfuric acid, 5 mL of the resulting culture solution was dispensed to each of five test tubes of 20 mm in diameter. The incubation was stopped at the point of 18 hours after the addition of glycine and levulinic acid. The accumulated amounts of 5-aminolevulinic acid and 5-amino-4-hydroxypentanoic acid after the incubation for 18 hours are shown in Table 3.

TABLE 2

| Medium 2 | Concentration (g/L) |
|---|---|
| Sodium L-glutamate monohydrate | 7.6 |
| $Na_2HPO_4$ | 1.73 |
| $NaH_2PO_4$ | 0.94 |
| $(NH_4)_2HPO_4$ | 1.6 |
| $MgSO_4 \cdot 7H_2O$ | 0.4 |
| $CaCl_2 \cdot 2H_2O$ | 0.106 |
| Mn-containing yeast extract | $10.9 \times 10^{-3}$ |
| Nicotinic acid | $2.0 \times 10^{-3}$ |
| (+)-Biotin | $2.0 \times 10^{-5}$ |
| Thiamine hydrochloride | $2.0 \times 10^{-3}$ |
| Yeast extract | 8 |
| $FeCl_3 \cdot 6H_2O$ | $5.44 \times 10^{-3}$ |
| Glucose | 45 |

Example 1

The same procedure as Comparative Example 1 was performed except that after incubating at 28° C. for 24 to 26 hours L-arginine was added so as to give its concentration of 0.5 mM. The accumulated amounts of 5-aminolevulinic acid and 5-amino-4-hydroxypentanoic acid when the incubation was stopped at the point of 18 hours after the addition of glycine and levulinic acid are shown in Table 3.

Example 2

The same procedure as Comparative Example 1 was performed except that after incubating at 28° C. for 24 to 26 hours, L-arginine was added so as to give a concentration of 1 mM. The accumulated amounts of 5-aminolevulinic acid and 5-amino-4-hydroxypentanoic acid when the incubation was stopped at the point of 18 hours after the addition of glycine and levulinic acid are shown in Table 3.

Example 3

The same procedure as Comparative Example 1 was performed except that after incubating at 28° C. for 24 to 26 hours, L-arginine was added so as to give a concentration of 2 mM. The accumulated amounts of 5-aminolevulinic acid and 5-amino-4-hydroxypentanoic acid when the incubation was stopped at the point of 18 hours after the addition of glycine and levulinic acid are shown in Table 3.

Example 4

The same procedure as Comparative Example 1 was performed except that after incubating at 28° C. for 24 to 26 hours, L-arginine was added so as to give a concentration of 5 mM. The accumulated amounts of 5-aminolevulinic acid and 5-amino-4-hydroxypentanoic acid when the incubation was stopped at the point of 18 hours after the addition of glycine and levulinic acid are shown in Table 3.

Example 5

The same procedure as Comparative Example 1 was performed except that after incubating at 28° C. for 24 to 26 hours, L-arginine was added so as to give a concentration of 10 mM. The accumulated amounts of 5-aminolevulinic acid and 5-amino-4-hydroxypentanoic acid when the incubation was stopped at the point of 18 hours after the addition of glycine and levulinic acid are shown in Table 3.

TABLE 3

| | At the point of stopping the incubation | | | |
|---|---|---|---|---|
| | Final concentration of added L-arginine (mM) | Accumulated amount of 5-amino-levulinic acid (mM) | Accumulated amount of 5-amino-4-hydroxy-pentanoic acid (mM) | Accumulated amount ratio of 5-aminolevulinic acid/5-amino-4-hydroxy-pentanoic acid (mM/mM) |
| Comparative Example 1 | 0 | 22.7 | 0.45 | 50.4 |
| Example 1 | 0.5 | 23.6 | 0.33 | 71.5 |
| Example 2 | 1 | 23.6 | 0.32 | 73.8 |
| Example 3 | 2 | 23.7 | 0.30 | 79.0 |
| Example 4 | 5 | 23.4 | 0.32 | 73.1 |
| Example 5 | 10 | 23.8 | 0.35 | 68.0 |

As is apparent from Table 3, addition of L-arginine improved the productivity of 5-aminolevulinic acid and increased the ratio of the accumulated amount of 5-aminolevulinic acid to that of 5-amino-4-hydroxypentanoic acid up to by about 60%.

Production Example 2

Medium 1 (200 mL) was placed in a 2-L conical flask and was sterilized at 121° C. for 20 min, followed by being cooled. *Rhodobacter sphaeroides* CR0072009 (FERM BP-6320) was inoculated in Medium 1. The mixture was incubated with shaking at 32° C. in a dark place for 26 hours.

The resulting culture was inoculated again in 200 mL of Medium 1 prepared in a 2-L conical flask such that the initial bacterial concentration (OD: 660 nm) was 0.4 and was subjected to incubation with agitation at 32° C. in a dark place for 20 hours.

Comparative Example 2

The culture obtained in Production Example 2 was inoculated in Medium 3 (1.8 L, formula is shown in Table 4) prepared in a 3-L culture vessel such that the initial bacterial concentration (OD: 660 nm) was 0.4 and was subjected to incubation with aeration and agitation at 28° C., in which the aeration rate was 1.8 L/min such that the lower limit of the dissolved oxygen concentration was 5%. Glycine and levulinic acid were added so as to give concentrations of 65 mM and 5 mM respectively at the point of 24 to 26 hours after the start of the incubation. The incubation was continued with agitation rotation speed of 420 rpm while maintaining pH in the range from 6.4 to 6.5 using sulfuric acid. Furthermore, glycine was added so as to give a concentration of 65 mM at every 12 hours' point (three times, after the point of 40 hours after the start of incubation, and the incubation was stopped at the point of 52 hours after the first addition of glycine. The accumulated amount of 5-aminolevulinic acid is shown in Table 5.

TABLE 4

| Medium 3 | Concentration (g/L) |
|---|---|
| Sodium L-glutamate monohydrate | 9.3 |
| $Na_2HPO_4$ | 1.73 |
| $NaH_2PO_4$ | 0.94 |
| $(NH_4)_2HPO_4$ | 1.6 |
| $MgSO_4 \cdot 7H_2O$ | 0.4 |

TABLE 4-continued

| Medium 3 | Concentration (g/L) |
| --- | --- |
| $CaCl_2 \cdot 2H_2O$ | 0.106 |
| Mn-containing yeast extract | $10.9 \times 10^{-3}$ |
| Nicotinic acid | $2.0 \times 10^{-3}$ |
| (+)-Biotin | $2.0 \times 10^{-5}$ |
| Thiamine hydrochloride | $2.0 \times 10^{-3}$ |
| Yeast extract | 7.5 |
| $FeCl_3 \cdot 6H_2O$ | $5.44 \times 10^{-3}$ |
| Glucose | 45 |

Example 6

The same procedure as Comparative Example 2 was performed except that after incubating at 28° C. for 24 to 26 hours, L-arginine was added so as to give a concentration of 5 mM. The accumulated amount of 5-aminolevulinic acid is shown in Table 5.

Example 7

The same procedure as Comparative Example 2 was performed except that after incubating at 28° C. for 24 to 26 hours, L-arginine was added so as to give a concentration of 7.5 mM. The accumulated amount of 5-aminolevulinic acid is shown in Table 5.

Example 8

The same procedure as Comparative Example 2 was performed except that after incubating at 28° C. for 24 to 26 hours, L-arginine was added so as to give a concentration of 10 mM. The accumulated amount of 5-aminolevulinic acid is shown in Table 5.

TABLE 5

| | Final concentration of added L-arginine (mM) | At the point of stopping the incubation Accumulated amount of 5-aminolevulinic acid (mM) |
| --- | --- | --- |
| Comparative Example 2 | 0 | 69.0 |
| Example 6 | 5 | 71.2 |
| Example 7 | 7.5 | 71.2 |
| Example 8 | 10 | 69.8 |

As is apparent from Table 5, addition of L-arginine increased the accumulated amount of 5-aminolevulinic acid.

Production Example 3

Medium 1 (200 mL) was placed in a 2-L conical flask and was sterilized at 121° C. for 20 min, followed by being cooled. *Rhodobacter sphaeroides* CR0072009 (FERN BP-6320) was inoculated in Medium 1. The mixture was incubated with shaking at 32° C. in a dark place for 26 hours.

The resulting culture was inoculated again in 200 mL of Medium 1 prepared in a 2-L conical flask such that the initial bacterial concentration (OD: 660 nm) was 0.4 and was subjected to incubation with agitation at 32° C. in a dark place for 20 hours.

Comparative Example 3

The culture obtained in Production Example 3 was inoculated in Medium 4 (1.8 L, formula is shown in Table 6) prepared in a 3-L culture vessel such that the initial bacterial concentration (OD: 660 nm) was 0.4. The mixture was subjected to incubation with aeration and agitation at 28° C., in which the aeration rate was 1.8 L/min such that the lower limit of the dissolved oxygen concentration was 5%. Glycine and levulinic acid were added so as to give concentrations of 65 mM and 5 mM, respectively, at the point of 24 to 26 hours after the start of the incubation, and the incubation was continued at an agitation rotation speed of 420 rpm while maintaining the pH in the range from 6.4 to 6.5 using sulfuric acid. Furthermore, glycine was added so as to give the concentration of 65 mM at the points of 40 hours and 52 hours after the start of the incubation, and the incubation was stopped 40 hours after the first addition of glycine. The accumulated amount of 5-aminolevulinic acid is shown in Table 7.

TABLE 6

| Medium 4 | Concentration (g/L) |
| --- | --- |
| Sodium L-glutamate monohydrate | 7.6 |
| $Na_2HPO_4$ | 1.73 |
| $NaH_2PO_4$ | 0.94 |
| $(NH_4)_2HPO_4$ | 1.6 |
| $MgSO_4 \cdot 7H_2O$ | 0.4 |
| $CaCl_2 \cdot 2H_2O$ | 0.106 |
| Mn-containing yeast extract | $10.9 \times 10^{-3}$ |
| Nicotinic acid | $2.0 \times 10^{-3}$ |
| (+)-Biotin | $2.0 \times 10^{-5}$ |
| Thiamine hydrochloride | $2.0 \times 10^{-3}$ |
| Yeast extract | 7 |
| $FeCl_3 \cdot 6H_2O$ | $5.44 \times 10^{-3}$ |
| Glucose | 45 |

Example 9

The same procedure as Comparative Example 3 was performed except that after the incubation at 28° C. for 24 to 26 hours, L-arginine was added so as to give the concentration of 4.5 mM. The accumulated amount of 5-aminolevulinic acid is shown in Table 7.

TABLE 7

| | Final concentration of added L-arginine (mM) | At the point of stopping the incubation Accumulated amount of 5-aminolevulinic acid (mM) |
| --- | --- | --- |
| Comparative Example 3 | 0 | 58.7 |
| Example 9 | 4.5 | 62.7 |

As is apparent from Table 7, addition of L-arginine improved the productivity of 5-aminolevulinic acid.

Comparative Example 4

Medium 1 (200 mL) was placed in a 2-L conical flask and was sterilized at 121° C. for 20 min, followed by being cooled. *Rhodobacter sphaeroides* CR0072009 (FERN BP-6320) was inoculated in Medium 1. The mixture was incubated with shaking at 32° C. in a dark place for 26 hours.

The resulting culture was inoculated again in 200 mL of Medium 1 prepared in a 2-L conical flask such that the initial bacterial concentration (OD: 660 nm) was 0.4 and was subjected to incubation with agitation at 32° C. in a dark place for 20 hours.

Comparative Example 4

The culture obtained in Production Example 4 was inoculated in Medium 5 (1.8 L, formula is shown in Table 8) prepared in a 3-L culture vessel such that the initial bacterial concentration (OD: 660 nm) was 0.4. The mixture was subjected to incubation with aeration and agitation at 28° C., in which the aeration rate was 1.8 L/min such that the lower limit of the dissolved oxygen concentration was 5%. Glycine and levulinic acid were added so as to give concentrations of 65 mM and 5 mM, respectively, at the point of 24 to 26 hours after the start of the incubation, and the incubation was continued at an agitation rotation speed of 420 rpm while maintaining a pH from 6.4 to 6.5 using sulfuric acid. Furthermore, glycine was added so as to give the concentration of 65 mM every 12 hours after the incubation for 40 hours, and the incubation was stopped 52 hours after the first addition of glycine. The accumulated amount of 5-aminolevulinic acid after the stop of the incubation is shown in Table 9. The productivity shown in Table 9 is expressed relative to the accumulated amount of 5-aminolevulinic acid in Comparative Example 4, defined as 100%.

TABLE 8

| Medium 5 | Concentration (g/L) |
| --- | --- |
| Sodium L-glutamate monohydrate | 7.6 |
| $Na_2HPO_4$ | 1.73 |
| $NaH_2PO_4$ | 0.94 |
| $(NH_4)_2HPO_4$ | 1.6 |
| $MgSO_4 \cdot 7H_2O$ | 0.4 |
| $CaCl_2 \cdot 2H_2O$ | 0.106 |
| Mn-containing yeast extract | $10.9 \times 10^{-3}$ |
| Nicotinic acid | $2.0 \times 10^{-3}$ |
| (+)-Biotin | $2.0 \times 10^{-5}$ |
| Thiamine hydrochloride | $2.0 \times 10^{-3}$ |
| Yeast extract | 7.5 |
| $FeCl_3 \cdot 6H_2O$ | $5.44 \times 10^{-3}$ |
| Glucose | 45 |

Example 10

The same procedure as that in Comparative Example 4 was performed except that the concentration of sodium L-glutamate monohydrate added to the medium was 8.4 g/L (concentration of L-glutamic acid: 44.9 mM). The accumulated amount of 5-aminolevulinic acid when the incubation was stopped, at 52 hours after the addition of glycine, is shown in Table 9.

Example 11

The same procedure as that in Comparative Example 4 was performed except that the concentration of sodium L-glutamate monohydrate added to the medium was 9.3 g/L (concentration of L-glutamic acid: 49.7 mM). The accumulated amount of 5-aminolevulinic acid when the incubation was stopped, at 52 hours after the addition of glycine, is shown in Table 9.

Example 12

The same procedure as that in Comparative Example 4 was performed except that the concentration of sodium L-glutamate monohydrate added to the medium was 11.4 g/L (concentration of L-glutamic acid: 60.9 mM). The accumulated amount of 5-aminolevulinic acid when the incubation was stopped at 52 hours, after the addition of glycine, is shown in Table 9.

TABLE 9

| | Concentration of sodium L-glutamate monohydrate (g/L) | Concentration of L-glutamic acid (mM) | Accumulated amount of 5-aminolevulinic acid (mM) | Productivity of 5-aminolevulinic acid (%) |
| --- | --- | --- | --- | --- |
| Comparative Example 4 | 7.6 | 40.6 | 65.7 | 100.0 |
| Example 10 | 8.4 | 44.9 | 67.5 | 102.7 |
| Example 11 | 9.3 | 49.7 | 69.0 | 105.0 |
| Example 12 | 11.4 | 60.9 | 70.2 | 106.8 |

As is apparent from Table 9, the productivity of 5-aminolevulinic acid was improved by increasing the concentration of L-glutamic acid.

Production Example 5

Medium 1 (200 mL) was placed in a 2-L conical flask and was sterilized at 121° C. for 20 min, followed by being cooled. *Rhodobacter sphaeroides* CR0072009 (FERM BP-6320) was inoculated in Medium 1. The mixture was incubated with shaking at 32° C. in a dark place for 24 hours.

The resulting culture was inoculated again in 200 mL of Medium 1 prepared in a 2-L conical flask such that the initial bacterial concentration (OD: 660 nm) was 0.2. The mixture was subjected to incubation with agitation at 32° C. in a dark place for 24 hours.

The resulting culture was inoculated in 30 mL of Medium 2 prepared in a 300-mL conical flask such that the initial bacterial concentration (OD: 660 nm) was 0.5. The mixture was subjected to incubation with agitation at 28° C. in a dark place for 24 to 26 hours. Subsequently, glycine and levulinic acid were added so as to give concentrations of 60 mM and 5 mM, respectively. After adjustment of pH in the range from 6.4 to 6.5 with sulfuric acid, 5 mL of the culture solution was dispensed to each of five test tubes of 20 mm in diameter. The incubation was stopped at 18 hours after the addition of glycine. When glycine and levulinic acid were added, any of a variety of amino acids was also added so as to give a concentration of 5 mM. The results are shown in Table 10. The production ratio shown in Table 10 is expressed relative to the accumulated amount of 5-aminolevulinic acid in the test system not containing amino acids, defined as 100%.

TABLE 10

| Added amino acid | Production ratio of 5-aminolevulinic acid (%) |
| --- | --- |
| No addition | 100.0 |
| Methionine | 95.5 |
| Lysine | 99.0 |
| Threonine | 100.2 |
| Ornithine | 99.8 |
| Citrulline | 98.7 |
| Arginine | 106.2 |

As is apparent from Table 9, the productivity of 5-aminolevulinic acid is improved in accordance with increased concentration of glutamic acid. In addition, as is apparent from Table 10, the productivity of 5-aminolevulinic acid is improved by arginine, whereas it is not improved by methionine, lysine, threonine, ornithine or citrulline.

Production Example 6

Medium 1 (200 mL) was placed in a 2-L conical flask and was sterilized at 121° C. for 20 min, followed by being cooled. *Rhodobacter sphaeroides* CR0072009 (FERM BP-6320) was inoculated in Medium 1. The mixture was incubated with shaking at 32° C. in a dark place for 26 hours. The resulting culture was inoculated again in 200 mL of Medium 1 prepared in a 2-L conical flask such that the initial bacterial concentration (OD: 660 nm) was 0.4 and the mixture was subjected to incubation with agitation at 32° C. in a dark place for 20 hours.

Comparative Example 5

The culture obtained in Production Example 6 was inoculated in 1.8 L of Medium 5 prepared in a 3-L culture vessel such that the initial bacterial concentration (OD: 660 nm) was 0.4. The mixture was subjected to incubation with aeration and agitation at 28° C., in which the aeration rate of 1.8 L/min such that the lower limit of the dissolved oxygen concentration was 5%. Glycine and levulinic acid were added so as to give concentrations of 65 mM and 5 mM, respectively, at the time of 24 to 26 hours after the start of the incubation, and the incubation was continued at an agitation rotation speed of 420 rpm while maintaining a pH of from 6.4 to 6.5 using sulfuric acid. Furthermore, glycine was added so as to give a concentration of 65 mM every 12 hours after the incubation for 40 hours, and the incubation was stopped 52 hours after the first addition of glycine. The accumulated amounts of 5-aminolevulinic acid and 5-amino-4-hydroxypentanoic acid are shown in Table 11.

Comparative Example 6

The same procedure as Comparative Example 5 was performed except that sodium L-glutamate monohydrate was added so as to give a concentration of 9.3 g/L. The accumulated amounts of 5-aminolevulinic acid and 5-amino-4-hydroxypentanoic acid are shown in Table 11.

Example 13

The same procedure as Comparative Example 6 was performed except that after the incubation for 24 to 26 hours, L-arginine was added so as to give a concentration of 5 mM. The accumulated amounts of 5-aminolevulinic acid and 5-amino-4-hydroxypentanoic acid are shown in Table 11.

Example 14

The same procedure as Comparative Example 6 was performed except that after the incubation for 24 to 26 hours, L-arginine was added so as to give the concentration of 7.5 mM. The accumulated amounts of 5-aminolevulinic acid and 5-amino-4-hydroxypentanoic acid are shown in Table 11.

Example 15

The same procedure as Comparative Example 6 was performed except that after the incubation for 24 to 26 hours, L-arginine was added so as to give the concentration of 10 mM. The accumulated amounts of 5-aminolevulinic acid and 5-amino-4-hydroxypentanoic acid are shown in Table 11.

TABLE 11

| | | | At the point of stopping the incubation | | |
| --- | --- | --- | --- | --- | --- |
| | Concentration of L-glutamic acid (mM) | Final concentration of added L-arginine (mM) | Accumulated amount of 5-aminolevulinic acid (mM) | Accumulated amount of 5-amino-4-hydroxypentanoic acid (mM) | Accumulated amount ratio of 5-aminolevulinic acid/5-amino-4-hydroxypentanoic acid (mM/mM) |
| Comparative Example 5 | 40.6 | 0 | 65.8 | 2.75 | 23.9 |
| Comparative Example 6 | 49.7 | 0 | 69.0 | 2.92 | 23.6 |
| Example 13 | 49.7 | 5 | 71.2 | 2.39 | 29.8 |
| Example 14 | 49.7 | 7.5 | 71.2 | 2.10 | 33.9 |
| Example 15 | 49.7 | 10 | 69.8 | 2.01 | 34.7 |

As is apparent from Table 11, addition of L-arginine improved the productivity of 5-aminolevulinic acid and also inhibited the accumulated amount of 5-amino-4-hydroxypentanoic acid at the point of 52 hours after the addition of glycine. As a result, the ratio of the accumulated amount of 5-aminolevulinic acid to that of 5-amino-4-hydroxypentanoic acid was increased up to by about 50%.

The invention claimed is:

1. A method for producing 5-aminolevulinic acid or a salt thereof, comprising:
    preparing culture medium by adding a yeast extract and separately adding glutamic acid or a salt thereof in an amount of 42 mM to 100 mM as the glutamic acid and L-arginine or a salt thereof in an amount of 0.01 mM to 30 mM as the L-arginine, and
    culturing a 5-aminolevulinic acid-producing microorganism in the medium to produce 5-aminolevulinic acid or a salt thereof,
    wherein the yeast extract is added in an amount of 5 to 10 g/L.

2. The method according to claim 1, wherein the L-arginine or the salt thereof is separately added in an amount of 0.5 mM to 15 mM as the L-arginine.

3. The method according to claim 1, wherein
    the 5-aminolevulinic acid-producing microorganism belongs to the genus *Rhodobacter*.

4. The method according to claim 1, wherein the 5-aminolevulinic acid-producing microorganism is *Rhodobacter sphaeroides* or a variant thereof.

5. The method according to claim 1, wherein the 5-aminolevulinic acid-producing microorganism is *Rhodobacter sphaeroides* CR-0072009 and is deposited under FERM BP-6320.

6. The method according to claim 1, wherein the glutamic acid or the salt thereof is separately added in an amount of 48 to 80 mM as the glutamic acid.

7. The method according to claim 2, wherein the glutamic acid or the salt thereof is separately added in an amount of 48 to 80 mM as the glutamic acid.

8. The method according to claim 1, further comprising adding glycine or levulinic acid to the medium.

9. The method according to claim 1, further comprising purifying the 5-aminolevulinic acid or the salt thereof.

* * * * *